United States Patent [19]

Schreiber et al.

[11] Patent Number: 4,622,172
[45] Date of Patent: Nov. 11, 1986

[54] ALKYL-SUBSTITUTED SPIROUNDECENONE DERIVATIVES, ORGANOLEPTIC UTILITY THEREOF AND PROCESSES FOR PREPARING SAME

[75] Inventors: William L. Schreiber, Jackson; William D. Gillaspey, Aberdeen; Futoshi Fujioka, Wanamassa; Marie R. Hanna, Hazlet, all of N.J.

[73] Assignee: International Flavors & Fragrances Inc., New York, N.Y.

[21] Appl. No.: 805,739

[22] Filed: Dec. 6, 1985

[51] Int. Cl.$^4$ .................. A61K 7/49; C07C 49/603
[52] U.S. Cl. ..................... 252/522 R; 252/174.11; 568/367; 568/345
[58] Field of Search .............. 252/522 R, 174.11; 568/374, 367, 345, 349

[56] References Cited

U.S. PATENT DOCUMENTS

| | | | |
|---|---|---|---|
| 3,341,601 | 9/1967 | Mertzweiller | 568/420 |
| 3,929,895 | 12/1975 | Hall | 568/345 |
| 3,962,147 | 6/1978 | Maurer et al. | 252/522 R |
| 4,052,457 | 10/1977 | Nagakura et al. | 568/367 |
| 4,203,925 | 5/1981 | Barton et al. | 252/522 R |
| 4,261,866 | 4/1981 | Barton et al. | 252/522 R |
| 4,281,204 | 7/1981 | Willis et al. | 568/374 |

OTHER PUBLICATIONS

Tanaka et al., Chem. Comm., pp. 188–189, (1967).
Nerdel et al., Ann. Chem., vol. 710, p. 90, (1967).

Primary Examiner—James H. Reamer
Attorney, Agent, or Firm—Arthur L. Liberman

[57] ABSTRACT

Described are alkyl-substituted spiroundecenone derivatives defined according to the structure:

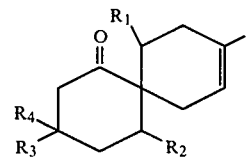

wherein $R_1$ represents isopropyl or hydrogen; $R_2$, $R_3$ and $R_4$ are the same and each represents methyl or hydrogen; with the provisos that:

(i) when $R_1$ is isopropyl, $R_2$, $R_3$ and $R_4$ are hydrogen; and (ii) when $R_2$, $R_3$ and $R_4$ are each methyl, $R_1$ is hydrogen, and uses thereof in augmenting or enhancing the aroma of perfume compositions, colognes and perfumed articles including but not limited to solid or liquid anionic, cationic, nonionic or zwitterionic detergents, fabric softener compositions, fabric softener articles and hair preparations; as well as processes for preparing said alkyl-substituted spiroundecenone derivatives.

9 Claims, 14 Drawing Figures

GLC PROFILE FOR EXAMPLE I
CRUDE

FIG. 2  NMR SPECTRUM FOR PEAK 10 OF FIG. 1, EXAMPLE I.

FIG. 3 NMR SPECTRUM FOR PEAK II OF FIG. 1, EXAMPLE I.

NMR SPECTRUM FOR PEAK 12 OF FIG.1, EXAMPLE I.

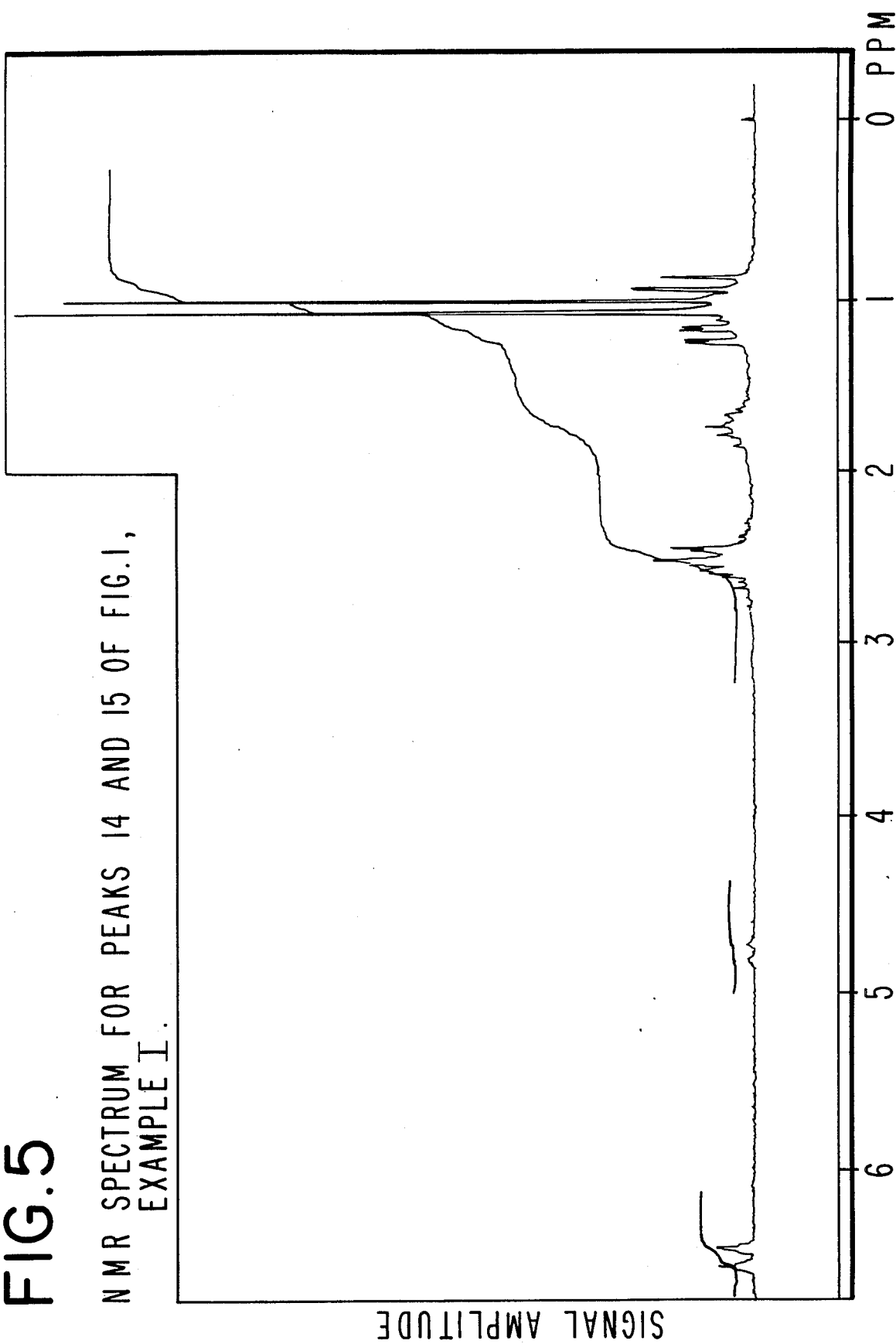

1ST DISTILLATION
GLC PROFILE FOR EXAMPLE II.

GLC PROFILE FOR EXAMPLE II, CRUDE

GLC PROFILE FOR BULKED DISTILLATION
FRACTIONS 9 AND 10, OF EXAMPLE II.
2ND DISTILLATION

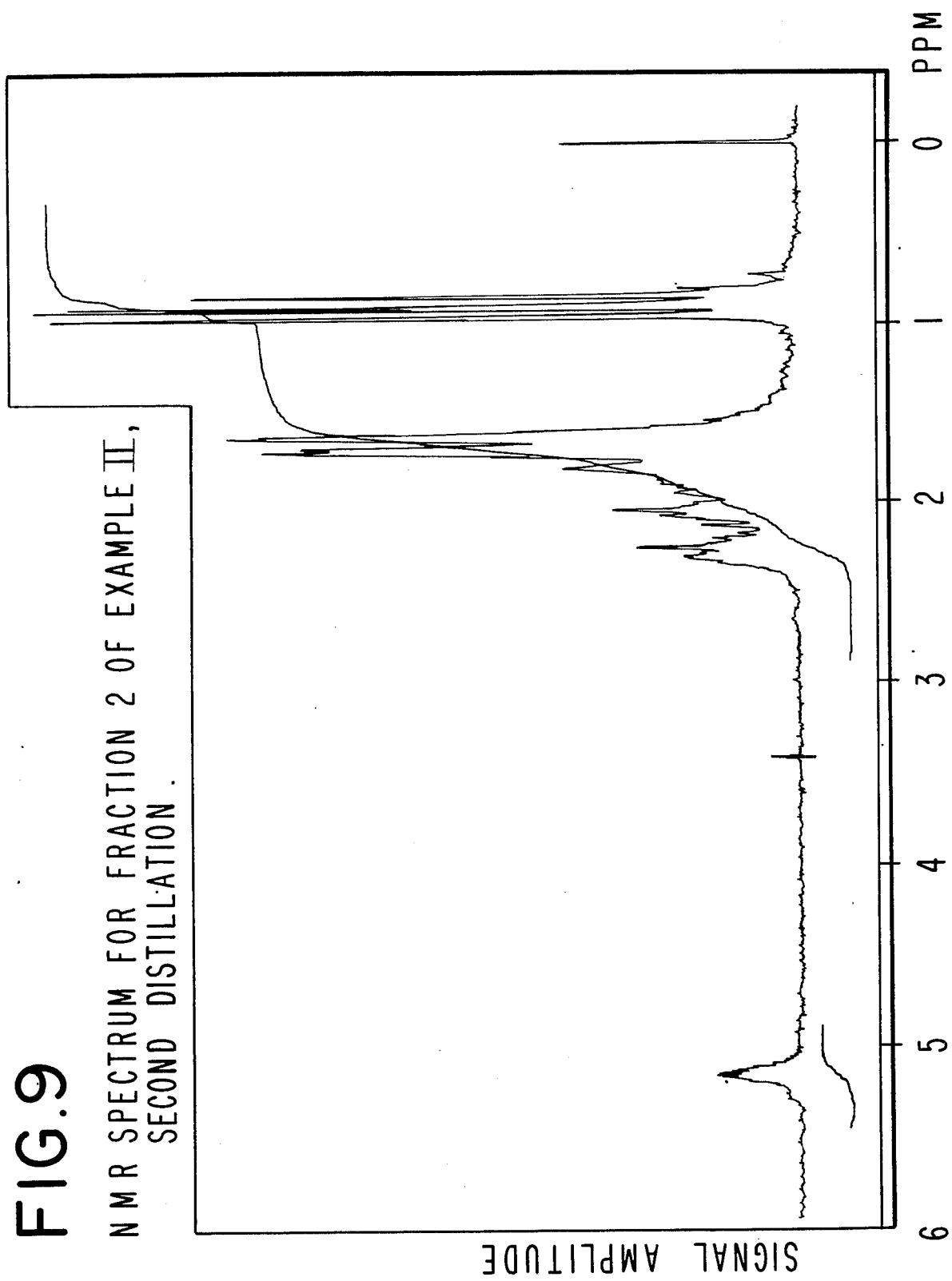
FIG. 9  NMR SPECTRUM FOR FRACTION 2 OF EXAMPLE II, SECOND DISTILLATION.

GLC PROFILE FOR EXAMPLE III
1st DISTILLATION PRODUCT

110

GLC PROFILE FOR EXAMPLE III. CRUDE

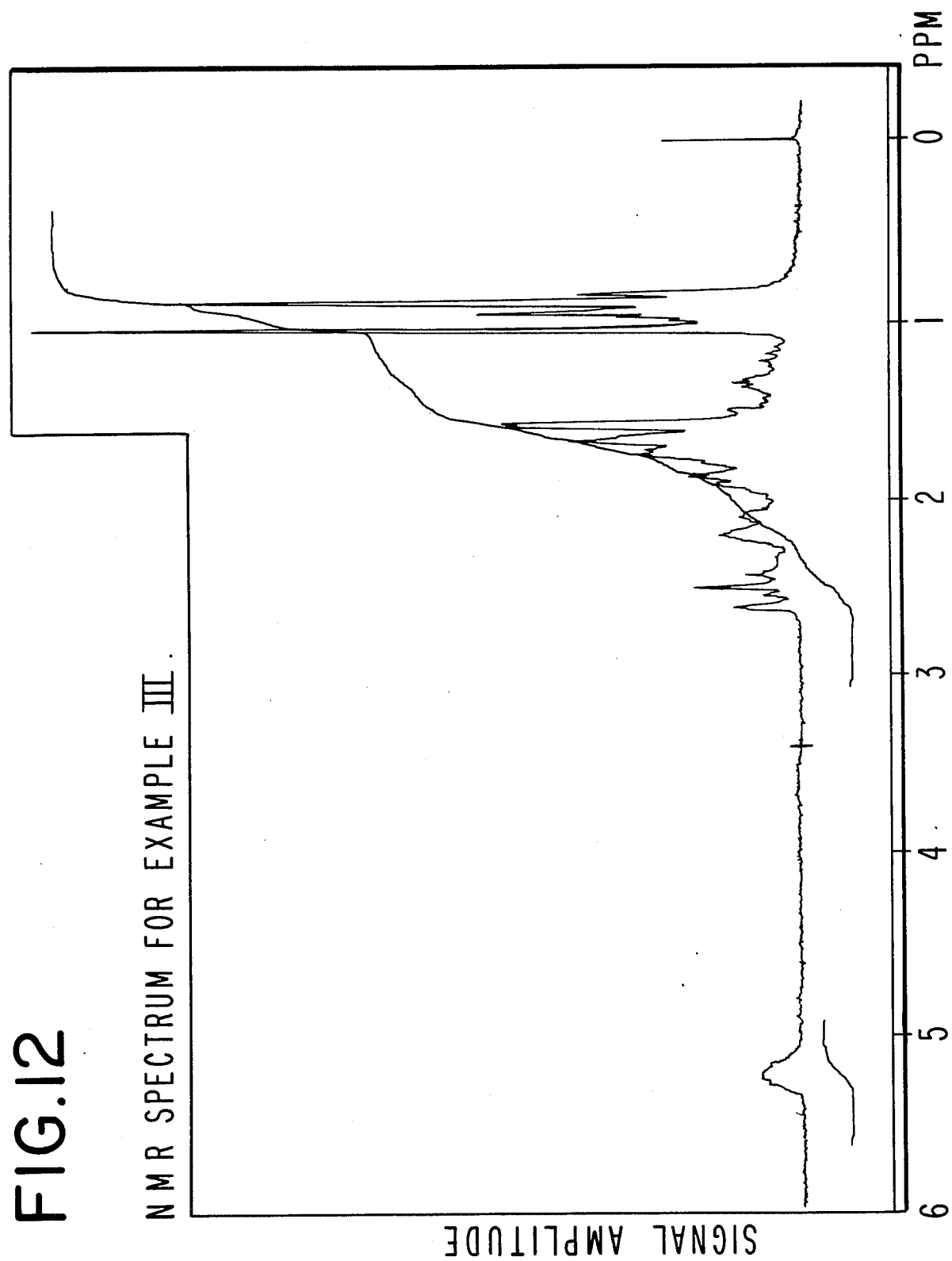
FIG. 12 NMR SPECTRUM FOR EXAMPLE III.

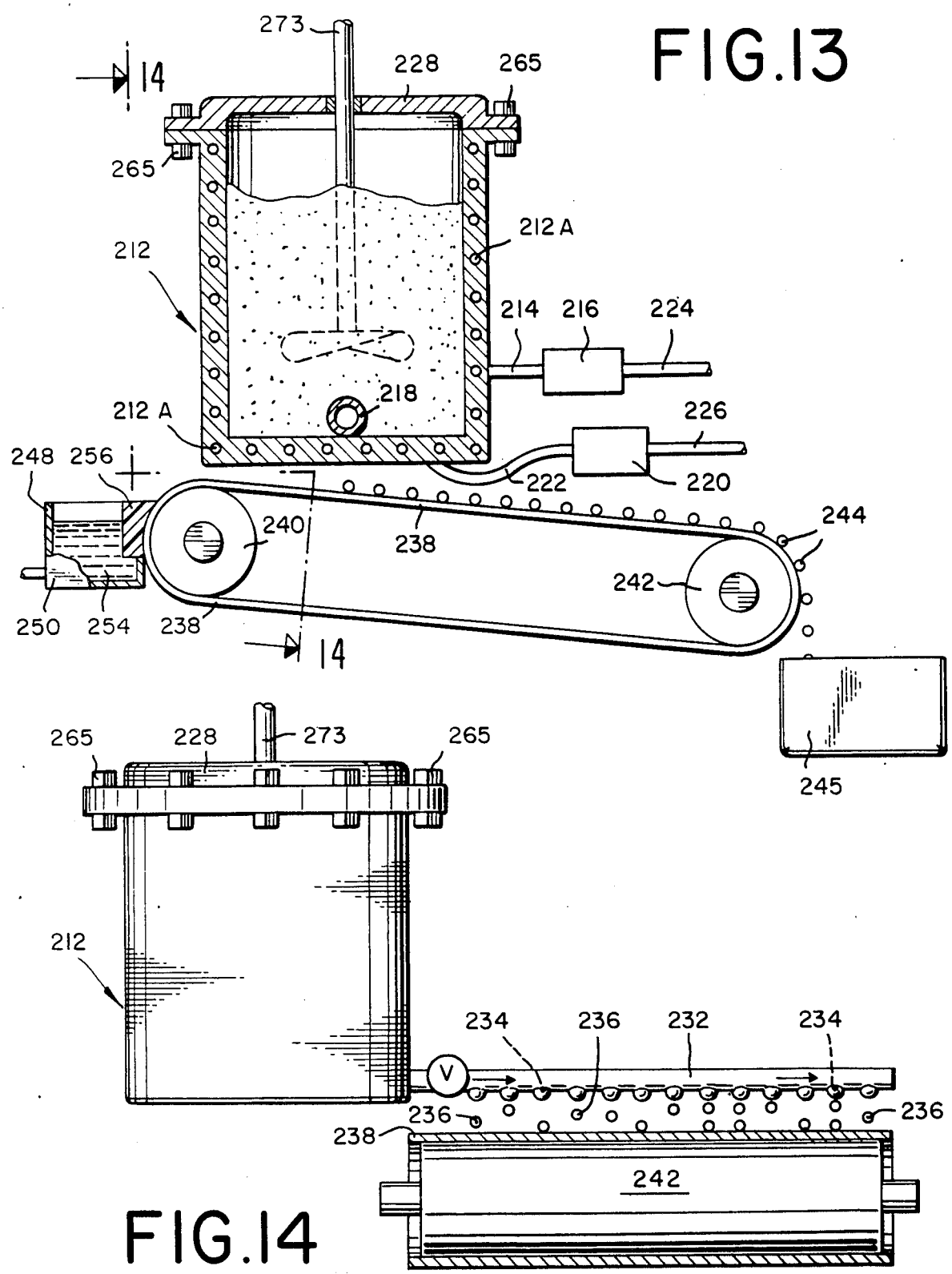

ALKYL-SUBSTITUTED SPIROUNDECENONE DERIVATIVES, ORGANOLEPTIC UTILITY THEREOF AND PROCESSES FOR PREPARING SAME

BACKGROUND OF THE INVENTION

The instant invention relates to alkyl-substituted spiroundecenone derivatives defined according to the structure:

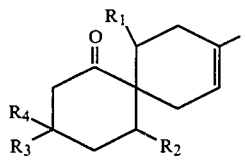

wherein $R_1$ represents isopropyl or hydrogen and $R_2$, $R_3$ and $R_4$ are each the same and each represents methyl or hydrogen; with the provisos:

(i) that when $R_1$ is isopropyl, $R_2$, $R_3$ and $R_4$ are hydrogen; and (ii) when $R_2$, $R_3$ and $R_4$ are methyl, $R_1$ is hydrogen, and uses of same in augmenting or enhancing the aroma of perfume compositions, perfumed articles and colognes.

Inexpensive chemical compounds which can provide woody, fruity, fresh minty, sweet, floral, herbaceous, spicy and celery aromas with pepper and geranium topnotes and tagette-like undertones are highly desirable in the art of perfumery. Many of the natural materials which provide such fragrances and contribute such desired nuances to perfume compositions as well as perfumed articles are high in cost, unobtainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Spiro ketones including spiroundecenones are known in the prior art and their utilities are known in perfumery.

Thus, Japanese Published Application No. 76/65738 (abstracted at Chemical Abstracts 85: 123440f) (corresponding to U.S. Pat. No. 4,052,457 issued on Oct. 4, 1977) discloses the compound having the structure:

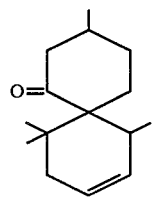

as being useful in perfumery and further discloses the process according to the reaction:

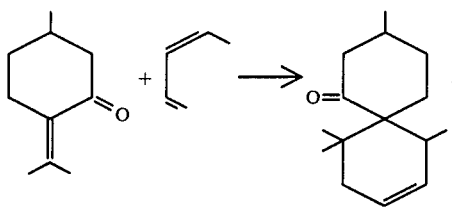

Nerdel and Dahl, *Ann. Chim.*, 710, 90 (1967) discloses the compound having the structure:

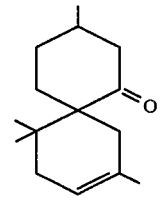

and the generic process, to wit:

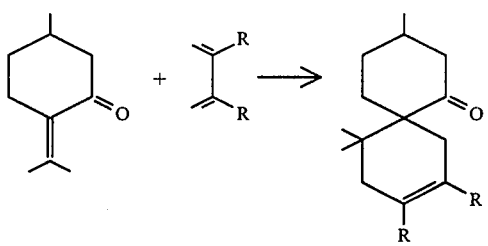

(wherein R represents hydrogen or methyl).

Tanaka, et al, Chem.Comm. 1967, page 188 (title of paper: "The Total Synthesis of Chamigrene" discloses the compound having the structure:

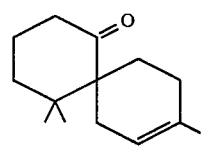

U.S. Pat. No. 4,261,866 issued on Apr. 14, 1981 discloses the genus of compounds having the structure:

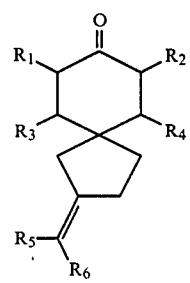

wherein $R_1$–$R_6$ each represents hydrogen or lower alkyl. U.S. Pat. No. 4,261,866 further discloses the broad genus, to wit:

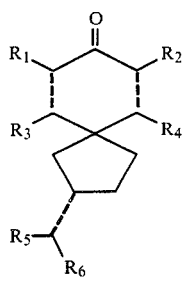

wherein each of the dashed lines represent carbon-carbon single bonds and carbon-carbon double bonds. The compounds disclosed in U.S. Pat. No. 4,261,866 are indicated to be useful in perfumery.

However, the alkyl-substituted spiroundecenone derivatives of our invention have unexpected, unobvious and advantageous perfumery properties when compared with the perfumery properties of the above-cited prior art.

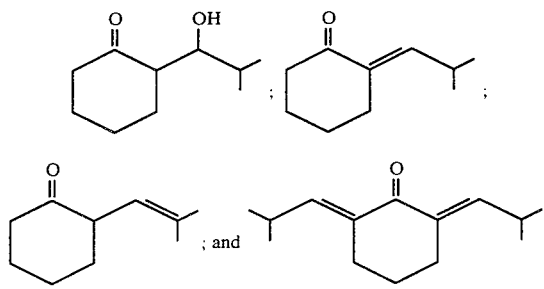

Figure 1:
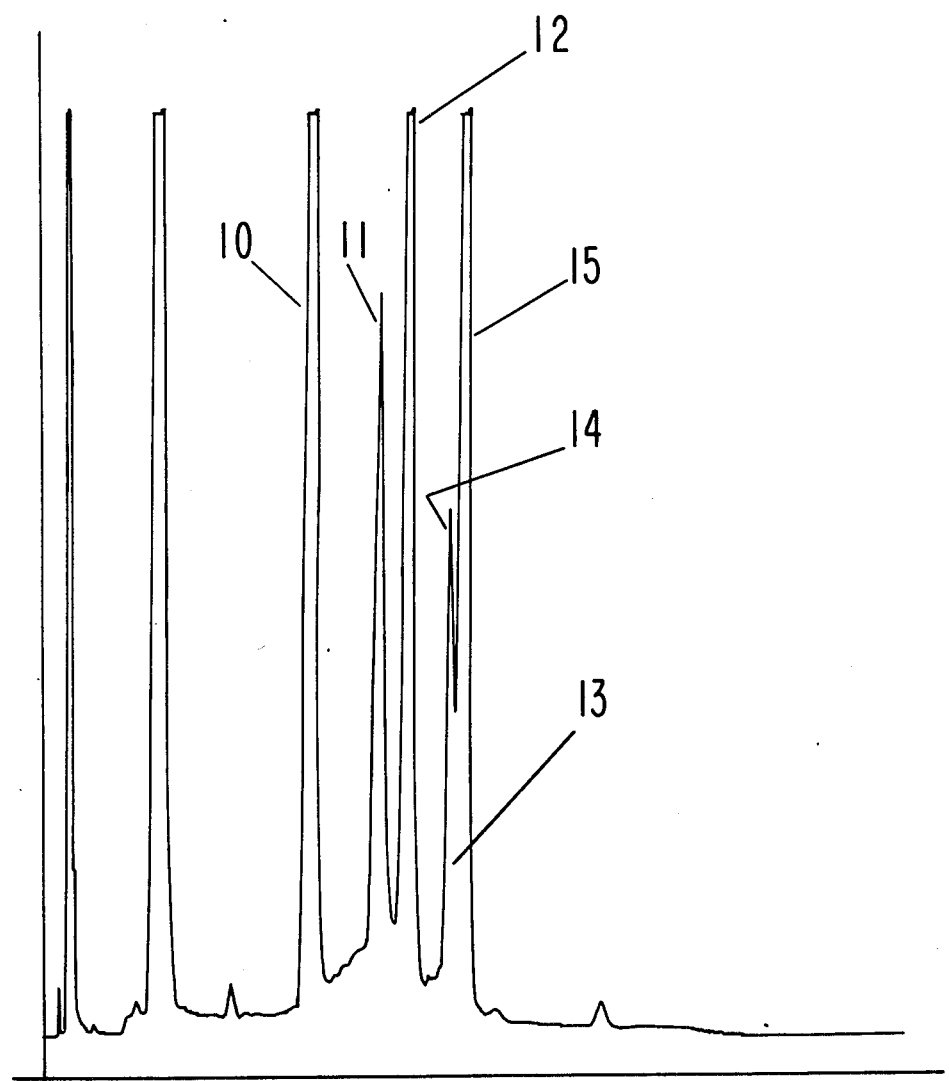
FIG. 1 is the GLC profile for the crude reaction product of Example I containing the compounds having the structures.
Figure 2:
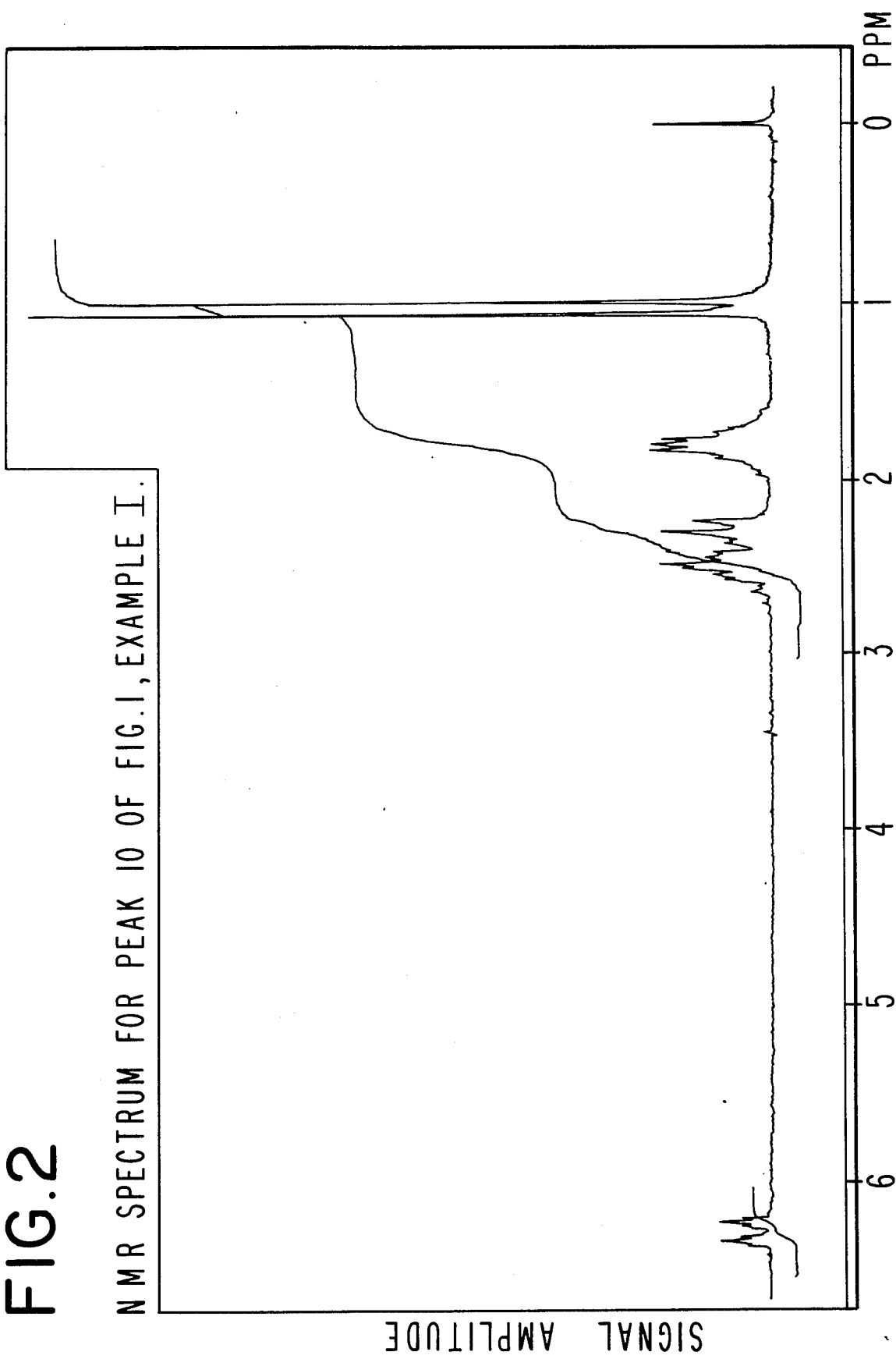

FIG. 2 is the NMR spectrum for the peak indicated by reference numeral 10 of the GLC profile of FIG. 1 for the compound having the structure:

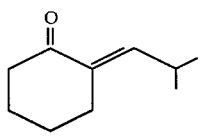

(Conditions: Field strength: 100 MHz; Solvent: CFCl$_3$).

Figure 3:
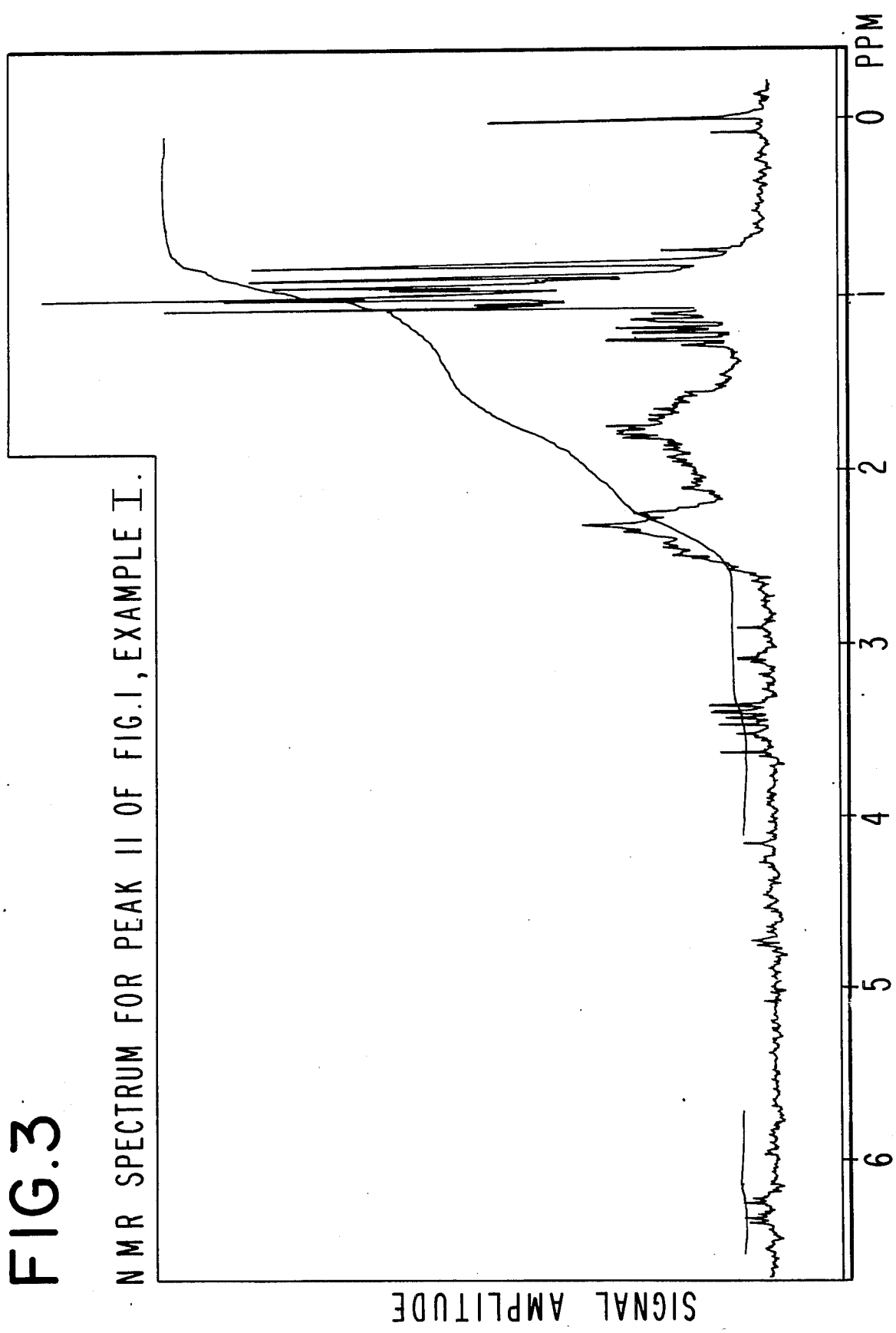

FIG. 3 is the NMR spectrum for the peak indicated by reference numeral 11 of the GLC profile of FIG. 1; for an isomer prepared according to the process of Example I (Conditions: Field strength: 100 MHz; Solvent: CFCl$_3$).

Figure 4:
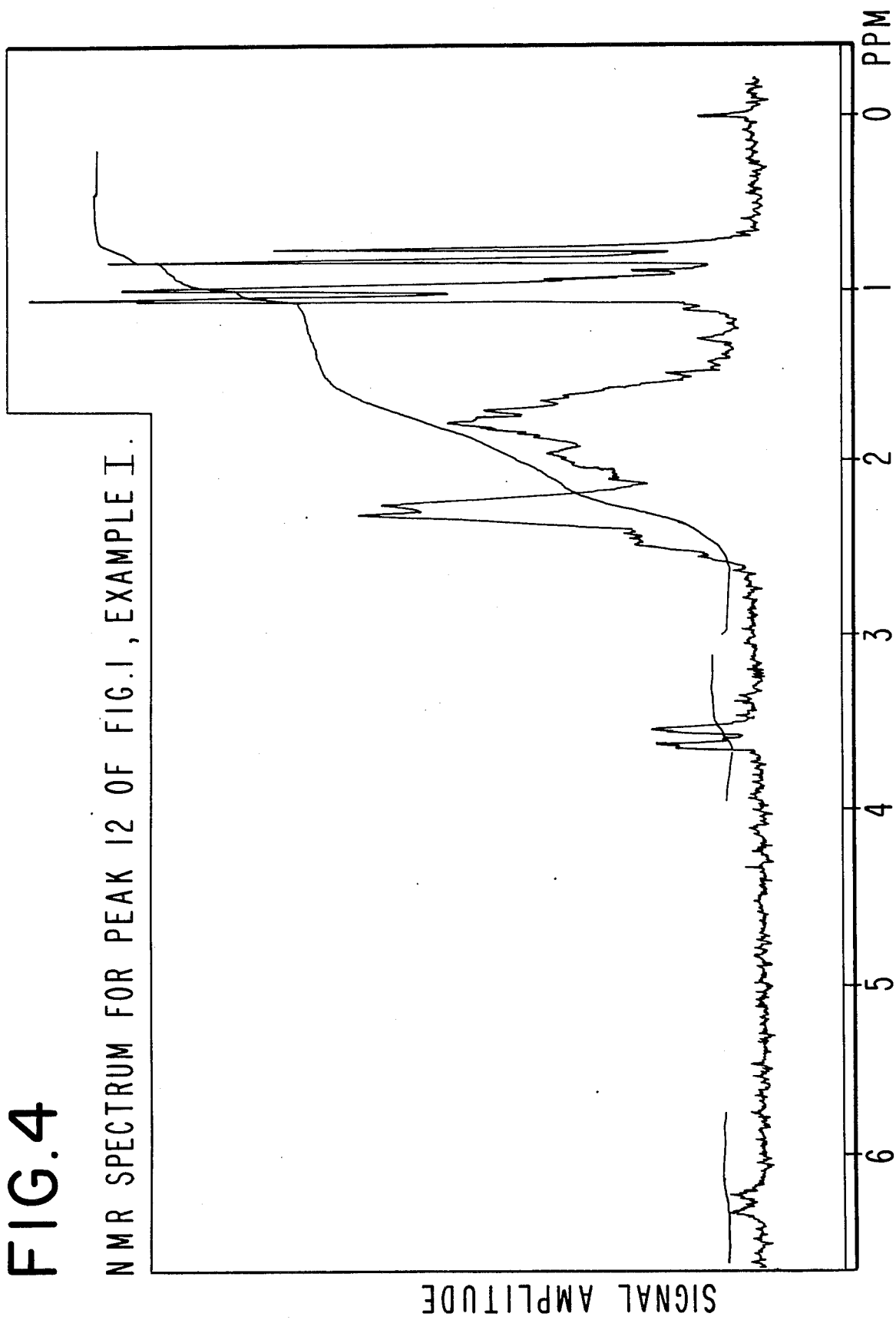

FIG. 4 is the NMR spectrum for the peak indicated by reference numeral 12 of the GLC profile of FIG. 1 containing the compound having the structure:

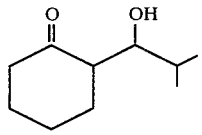

(Conditions: Field strength: 100 MHz; Solvent: CFCl$_3$).

FIG. 5 is the NMR spectrum for the peaks indicated by reference numerals 14 and 15 of the GLC profile of FIG. 1; which contains the compound having the structure:

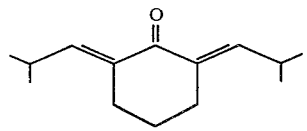

(Conditions: Field strength: 100 MHz; Solvent: CFCl$_3$).

Figure 6:
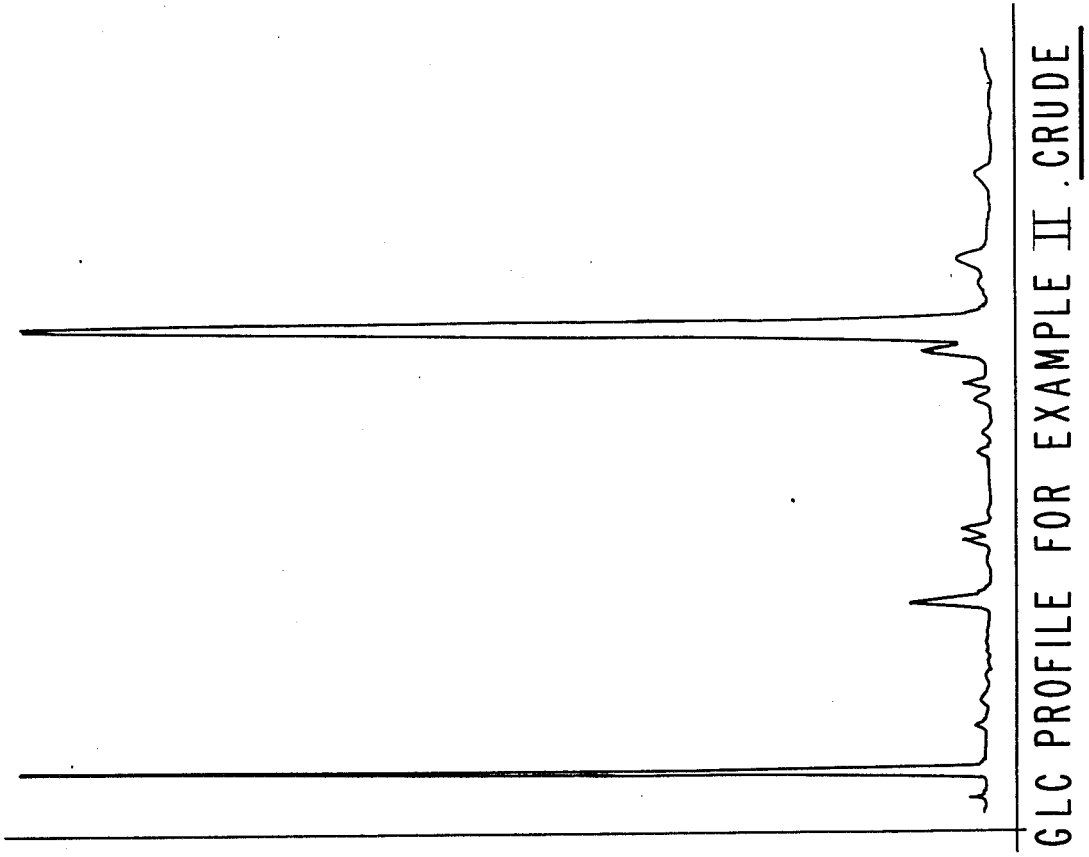

FIG. 6 is the GLC profile for the crude reaction product of Example II containing the compound having the structure:

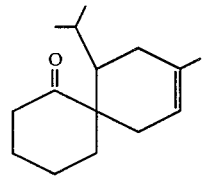

Figure 7:
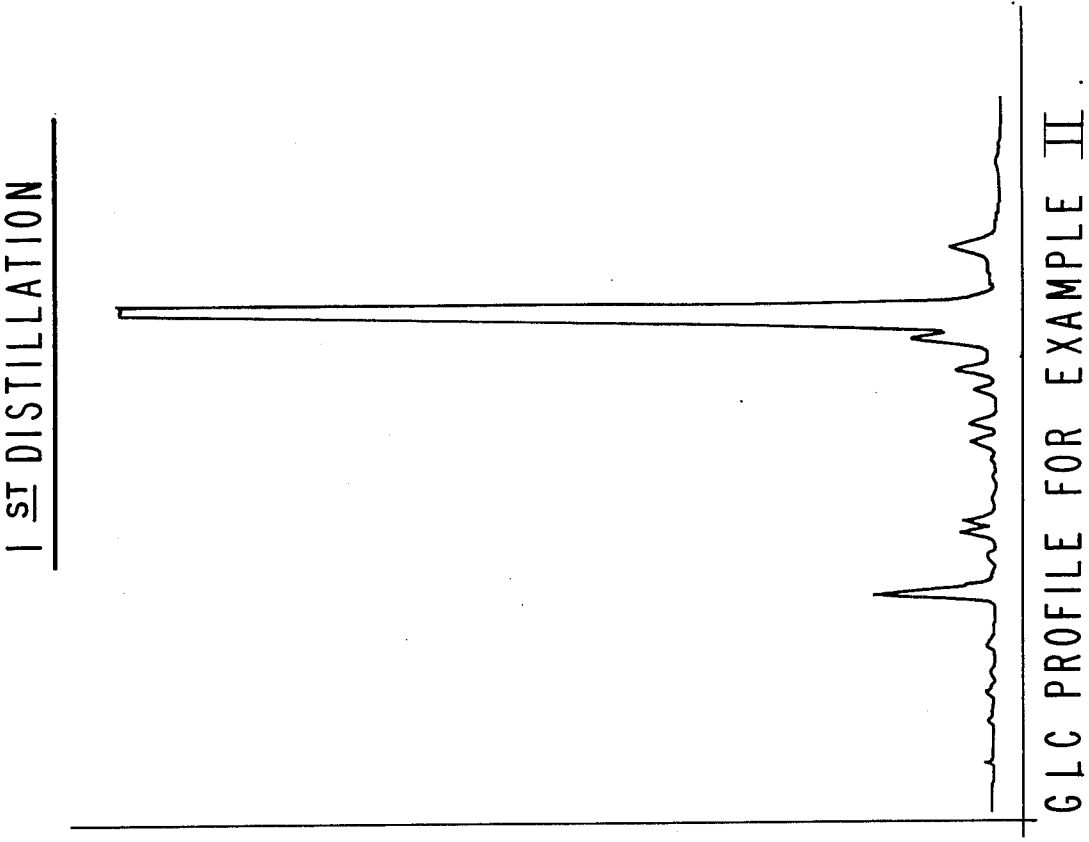

FIG. 7 is the GLC profile for the first distillation product of the reaction product of Example II containing the compound having the structure:

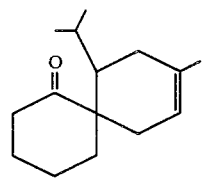

(Conditions: Carbowax column programmed at 100°–220° C. at 8° C. per minute).

Figure 8:
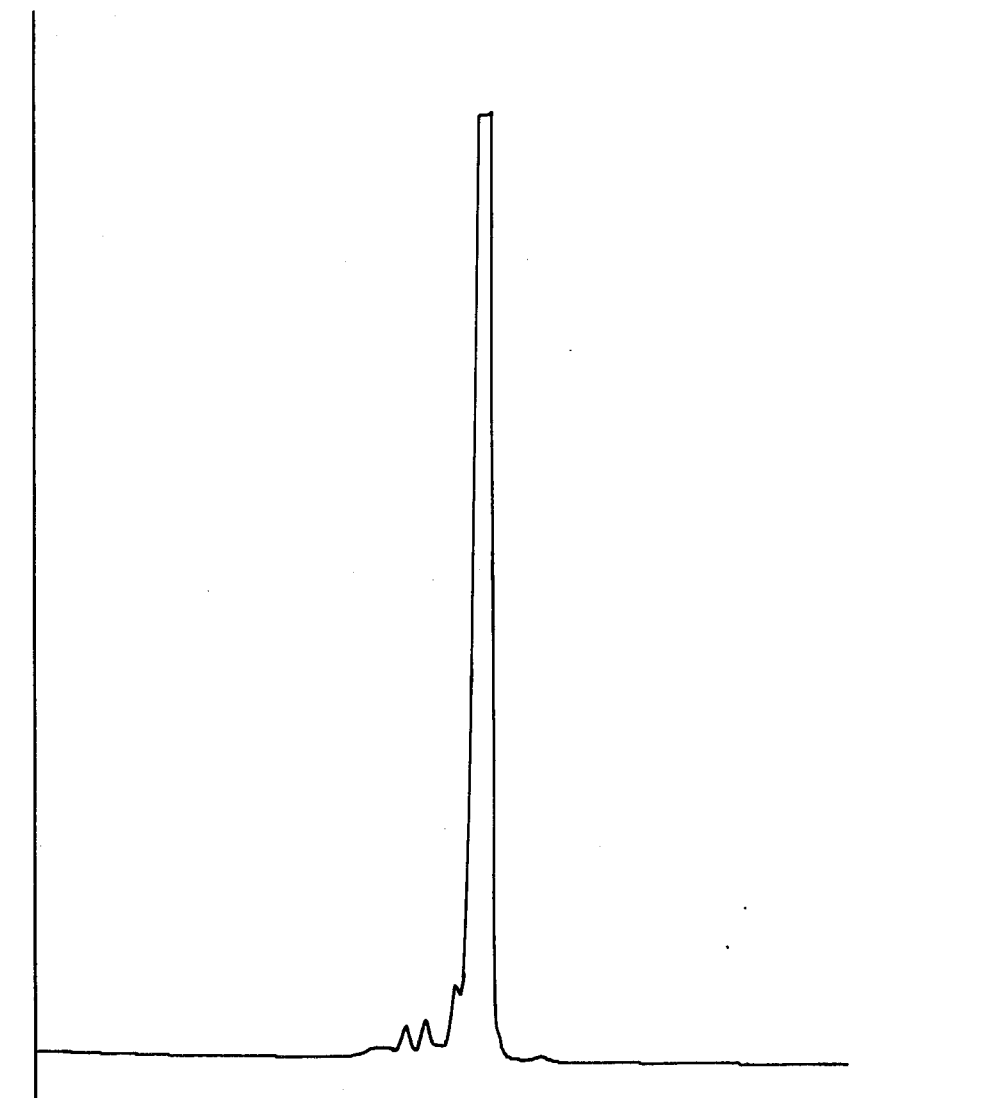

FIG. 8 is the GLC profile for bulked distillation Fractions 9 and 10 of the second distillation of the reaction product of Example II containing the compound having the structure:

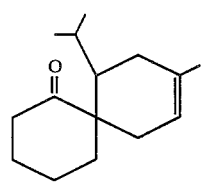

(Conditions: Carbowax 20M column programmed at 100°–220° C. at 8° C. per minute).

FIG. 9 is the NMR spectrum for Fraction 2 of the second distillation of the reaction product of Example II containing the compound having the structure:

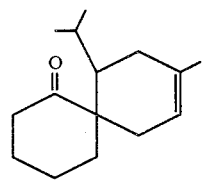

(Conditions: Field strength: 100 MHz; Solvent: CFCl$_3$).

Figure 10:
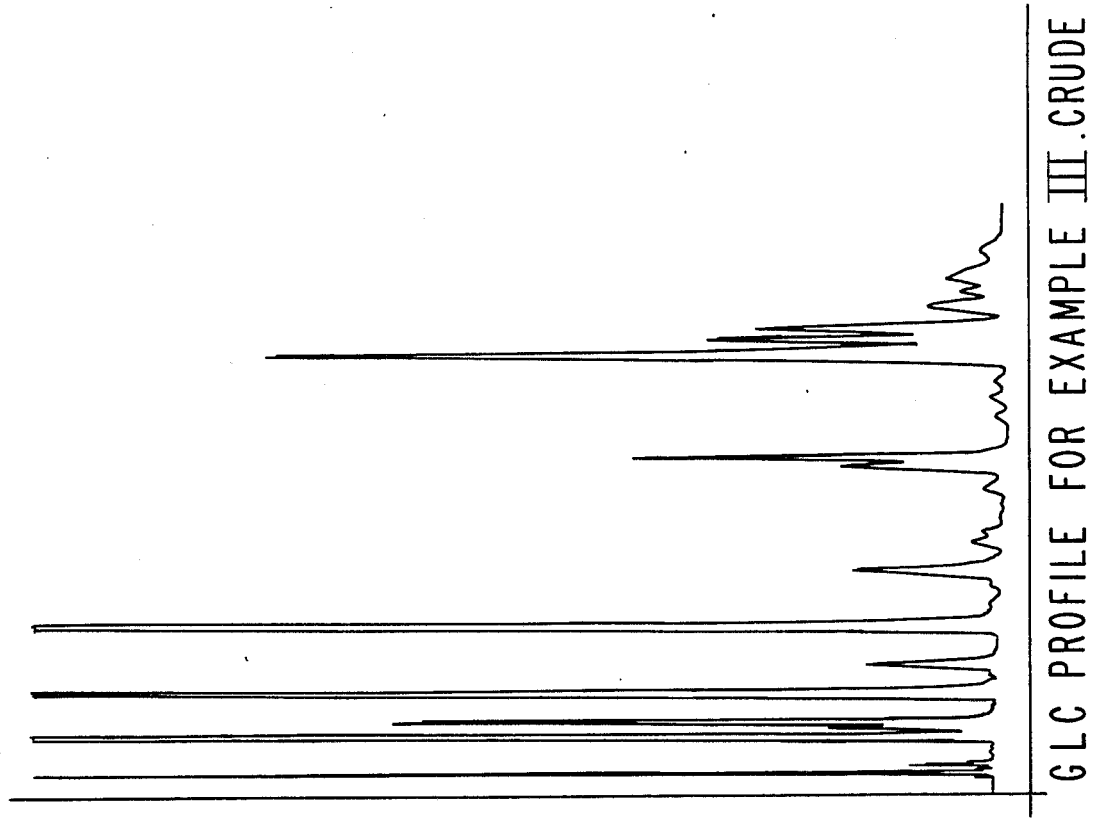

FIG. 10 is the GLC profile for the crude reaction product of Example III containing the compound having the structure:

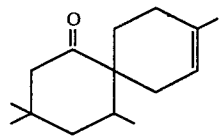

(Conditions: Carbowax column programmed at 100°-220° C. at 8° C. per minute).

Figure 11:
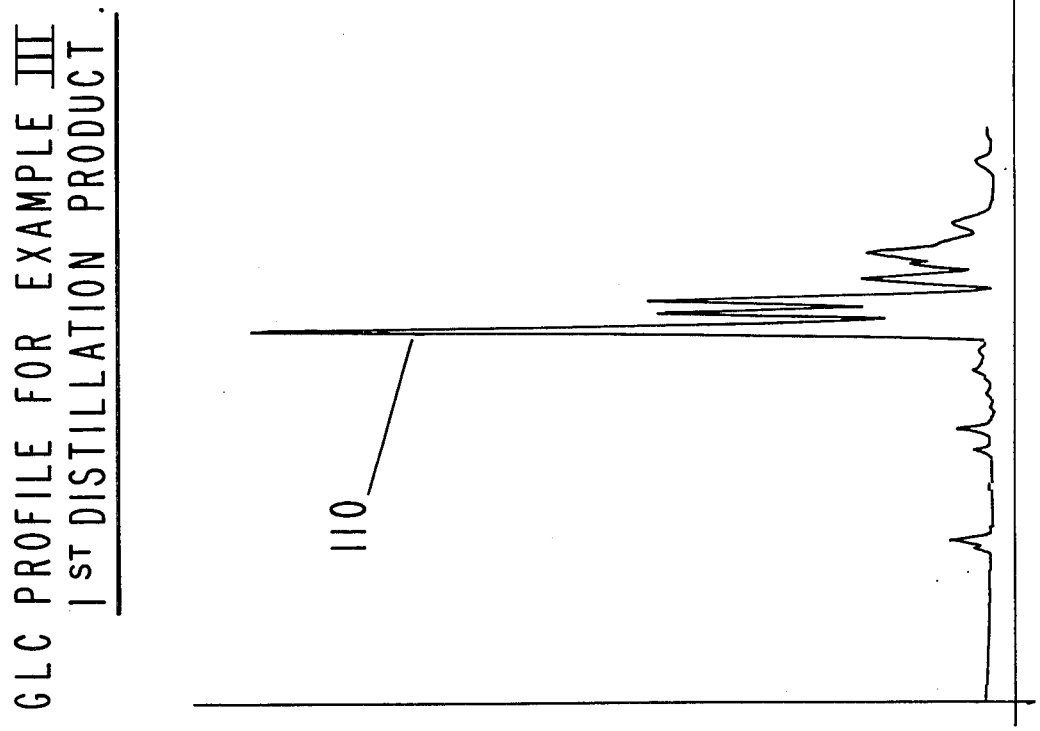

FIG. 11 is the GLC profile for the first distillation product of the reaction product of Example III containing the compound having the structure:

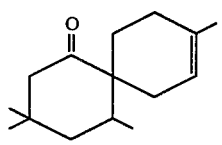

(Conditions: Carbowax 20M column programmed at 100°-220° C. at 8° C. per minute).

FIG. 12 is the NMR spectrum for the distilled reaction product of Example III containing the compound having the structure:

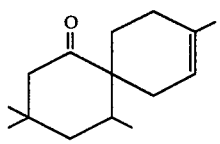

(Conditions: Field strength: 100 MHz; Solvent: CFCl₃).

FIG. 13 is a partial side elevation and partial sectional view of an apparatus for forming polymer pellets containing at least one of the alkyl-substituted spiroundecenone derivatives of our invention.

FIG. 14 is a section taken along the line 14—14 of FIG. 13.

DETAILED DESCRIPTION OF THE DRAWINGS

FIG. 1 is the GLC profile for the crude reaction product of Example I. The peak indicated by reference numeral 10 is the peak for the compound having the structure:

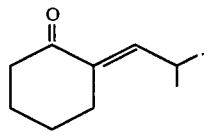

The peak indicated by reference numeral 11 is the peak for a mixture of compounds containing in a major proportion an optical isomer of the compound having the structure:

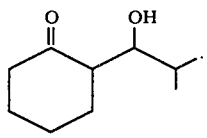

The peak indicated by reference numeral 12 is the peak for another optical isomer of the compound having the structure:

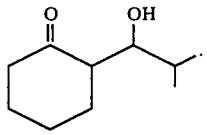

The peak indicated by reference numeral 13 which includes peaks 14 and 15 is for a mixture of compounds having as its major ingredient the compound having the structure:

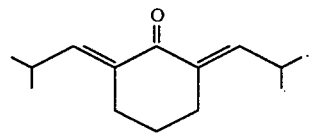

FIG. 11 is the GLC profile for the first distillation product of the reaction product of Example III. The peak indicated by reference numeral 110 is the peak for the compound having the structure:

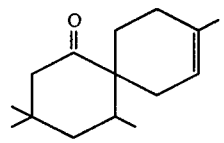

(Conditions: Carbowax 20M column programmed at 100°-220° C. at 8° C. per minute).

Referring to FIGS. 13 and 14, the apparatus used in producing polymeric fragrances containing the alkyl-substituted spiroundecenone derivatives of our invention comprises a device for forming scented polyolefin (for example) pellets, which comprises a vat or container 212 into which a mixture of polyolefin such as polyethylene and an aromatic substance or scented material is placed (in this case at least one of the alkyl-substituted spiroundecenone derivatives of our invention). The container is closed by an air-tight lid 228 and clamped to the container by bolts 265. A stirrer 273 traverses the lid or cover 228 in air-tight manner and is rotated in a suitable manner. A surrounding cylinder 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with viscosity ranging between 180 and 220 saybolt seconds and having a melting point in the range of 200°-280° F. The heater 212A is operated to maintain the upper portion of the container 212 within a temperature range of from 250°–350° F. The bottom portion of the container is heated by means of heating coils 212A heated through a control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (at least one of the alkyl-substituted spiroundecenone derivatives of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (containing at least one of the alkyl-substituted spiroundecenone derivatives of our invention) are added to the polyolefin.

After the scent imparting material (e.g., a composition containing at least one of the alkyl-substituted spiroundecenone derivatives of our invention, or one of the alkyl-substituted spiroundecenone derivatives of our invention taken alone) is added to the container 212, the mixture is stirred for a few minutes, for example, 5–15 minutes and maintained within the temperature range as indicated previously by heating coils 212A. The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter the valve "V" is opened permitting the mass to flow outwardly through conduit 218/232 having a multiplicity of orifices 234 adjacent to the lower side thereof. The outer end of the conduit 218/232 is closed so that the liquid polymer (e.g., polyolefin) and aroma imparting material (e.g., at least one of the alkyl-substituted spiroundecenone derivatives of our invention) will continuously drop through orifices 234 downwardly from conduit 232. During this time the temperatureof the polymer (e.g., polyolefin) and scent imparting material (e.g., a mixture containing at least one of the alkyl-substituted spiroundecenone derivatives of our invention) is accurately controlled so that a temperature in the range of from about 210°–275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the alkyl-substituted spiroundecenone derivatives of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic but a moistening means 248 insures a sufficiently cold temperature of the belt surface for adequate formation of the pellets 244. The adequate moistening means comprises a container 250 which is continuously fed with water 254 to maintain a level for moistening a sponge element 256 which bears against the exterior of the belt 238.

THE INVENTION

The present invention provides alkyl-substituted spiroundecenone derivatives defined according to the generic structure:

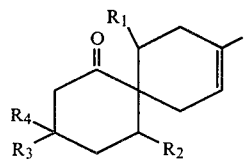

wherein R represents isopropyl or hydrogen; and $R_2$, $R_3$ and $R_4$ are each the same and each represents methyl or hydrogen with the provisos that:

(i) when $R_1$ is isopropyl then $R_2$, $R_3$ and $R_4$ each represents hydrogen; and (ii) when $R_2$, $R_3$ and $R_4$ are each methyl then $R_1$ represents hydrogen.

The compositions of matter of our invention produced according to the processes of our invention are capable of augmenting, enhancing or providing woody, fruity, fresh minty, sweet, floral, herbaceous, spicy and celery aromas with pepper and geranium topnotes and tagette-like undertones to perfume compositions, colognes and perfumed articles (e.g., solid or liquid anionic, cationic, nonionic or zwitterionic detergents, fabric softener articles, drier-added fabric softener articles, fabric softener compositions, cosmetic powders, hair preparations and perfumed polymers and the like).

The substances of our invention are first prepared by reacting the compound cyclohexenone with isobutyraldehyde via an "aldol" condensation reaction, first forming the compound having the structure:

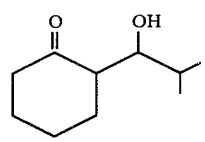

and then by means of dehydrating same forming the compound having the structure:

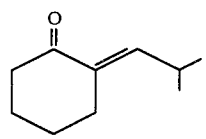

according to the reaction:

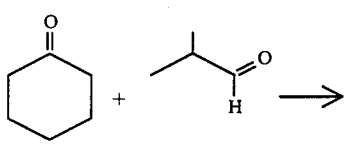

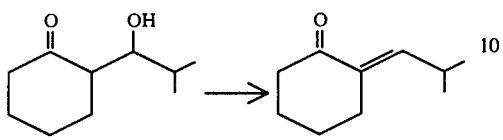

with the by-products having the structures:

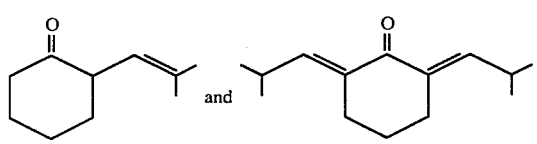

also being formed. The compound having the structure:

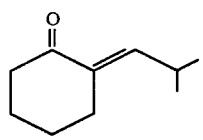

is then reacted with isoprene in order to form the compound having the structure:

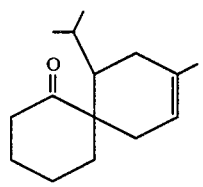

according to the reaction:

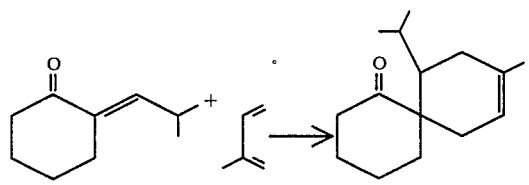

Alternatively, isophorone is reacted with isoprene and formaldehyde according to the reaction:

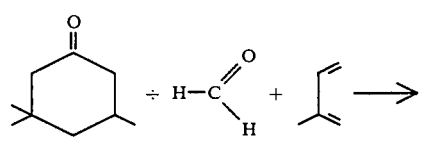

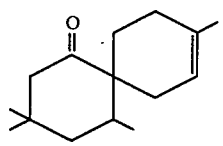

whereby the compound having the structure:

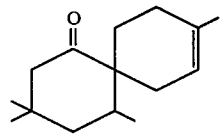

is formed.
The reaction:

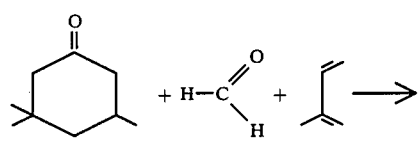

takes place in the presence of a Lewis acid catalyst such as aluminum trichloride and in the presence of an inert solvent, e.g., toluene at a temperature in the range of from about 30° up to about 50° C. (preferably at 40° C.). The mole ratio of isoprene to the compound having the structure:

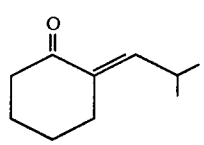

is about 1:1 with an excess of toluene being present. The amount of Lewis acid (e.g., aluminum chloride) in the reaction mass is between about 10 and 15% by weight of the reaction mass. It is preferred that the isoprene be in slight excess in the reaction mass, e.g., from about 3 up to about 10% in excess. The amount of inert solvent, e.g., in the reaction mass may vary from about 40% up to about 150% of the reaction mass.
In carrying out the reaction:

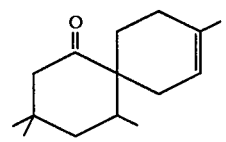

this reaction is carried out at a temperature in the range of from about 150° up to about 180° C. for a time of from about 2 hours up to about 10 hours. The reaction is carried out in the presence of dibutylamine. The reaction is carried out in two stages. In the second stage, acetic acid or a like low ionization constant acid is present in the reaction mass whereby the cyclization is completed to form the compound having the structure:

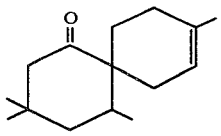

The ratio of the dihydroisophorone to formaldehyde and isoprene is in the range of about 1:1:1 with a slight molar excess of isoprene being present in the reaction mass. The weight ratio of dibutylamine to the dihydroisophorone is about 1:1. In the second stage of the reaction, the weight ratio of the acetic acid to the dihydroisophorone is about 1:1.

At the end of both reactions, the reaction masses are respectively washed (e.g., with sodium chloride solution) until neutral and then fractionally distilled to yield odor acceptable material.

Examples of the alkyl-substituted spiroundecenone derivatives of our invention are set forth in the following Table I.

TABLE I

| Alkyl-Substituted Spiroundecenone Derivatives Of Our Invention | Perfumery Properties |
|---|---|
| The compound having the structure: <br><br> prepared according to Example II, bulked distillation Fractions 4–8. | A woody, fruity, minty and floral aroma with pepper and geranium topnotes. |
| The compound having the structure: <br><br> prepared according to Example III, bulked distillation Fractions 6–8. | A woody, fresh minty, sweet, herbaceous, spicy and celery aroma with tagette-like undertones. |

One or more of the alkyl-substituted spiroundecenone derivatives prepared in accordance with the processes of our invention and one or more auxiliary perfume ingredients including, for example, alcohols, aldehydes, ketones other than the alkyl-substituted spiroundecenone derivatives of our invention, terpenic hydrocarbons, nitriles, esters, lactones, natural essential oils and synthetic essential oils may be admixed so that the combined odors of the individual components produce a pleasant and desired fragrance, particularly and preferably in the woody, minty, herbaceous, spicy and tagette fragrances. Such compositions usually contain:

(a) the main note or the "bouquet" or foundation stone of the composition;
(b) modifiers which round-off and accompany the main note;
(c) fixatives which include odorous substances which lend a particular note to the perfume throughout all stages of evaporation and substances which retard evaporation; and
(d) topnotes which are usually low boiling, fresh smelling materials.

In perfume compositions, it is the individual components which contribute their particular olfactory characteristics, however, the overall sensory effect of the perfume composition will be at least the sum total of the effects of each of the ingredients. Thus, the alkyl-substituted spiroundecenone derivatives prepared in accordance with the processes of our invention can be used to alter, modify or enhance the aroma characteristics of a perfume composition, for example, by utilizing or moderating the olfactory reaction contributed by another ingredient in the composition.

The amount of the alkyl-substituted spiroundecenone prepared in accordance with the process of our invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of the alkyl-substituted spiroundecenone derivatives prepared in accordance with the processes of our invention or even less (e.g., 0.005%) can be used to impart, augment or enhance woody, fruity, fresh minty, sweet, floral, herbaceous, spicy and celery aromas with pepper and geranium topnotes and tagette-like undertones to soaps, cosmetics, anionic, cationic, nonionic or zwitterionic detergents, fabric softener compositions, fabric softener articles, microporous polymers, particularly acrylic resins, polyethylenes and other products. The amount employed can range up to 70% of the fragrance components and will depend on considerations of cost, nature of the end product, the effect desired on the finished product and the particular fragrance sought.

The alkyl-substituted spiroundecenone derivatives prepared in accordance with the processes of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens; powders, such as talcs, dusting powders, face powders, microporous "perfumed" slow release polymers and the like.

When used as (an) olfactory component(s) in perfumed articles, as little as 0.005% of the alkyl-substituted spiroundecenone derivatives prepared in accordance with the processes of our invention will suffice to impart, augment or enhance woody, fruity, fresh minty, sweet, floral, herbaceous, spicy and celery aromas with pepper and geranium topnotes and tagette-like undertones. Generally, no more than 6% of the alkyl-substituted spiroundecenone derivatives of our invention based on the ultimate end product is required in the perfumed article. Accordingly, the range of use of the alkyl-substituted spiroundecenone derivatives of our invention in perfumed articles, per se, is from about 0.005% up to about 6% by weight based on the perfumed article.

In addition, the perfume composition or fragrance composition of our invention can contain a vehicle or carrier for the alkyl-substituted spiroundecenone derivatives prepared in accordance with the processes of our invention. The vehicle can be a liquid such as a non-toxic alcohol, e.g., ethyl alcohol, a non-toxic glycol, e.g., propylene glycol or the like. The carrier can be an absorbent solid such as a gum (e.g., gum arabic, guar gum or xanthan gum or combination thereof) or components for encapsulating the composition (such as gelatin as by coacervation) or using prepolymers such as urea-formaldehyde prepolymers which are able to form a urea-formaldehyde polymer capsule around a liquid perfume center.

It will thus be apparent that the alkyl-substituted spiroundecenone derivatives prepared in accordance with the processes of our invention can be utilized to alter, modify or enhance sensory properties particularly organoleptic properties such as fragrances of a wide variety of consumable materials.

The following Examples I-III set forth means for preparing the alkyl-substituted spiroundecenone derivatives of our invention. The examples including and following Examples IV set forth illustrations of organoleptic utilities of the alkyl-substituted spiroundecenone derivatives of our invention.

All parts and percentages given herein are by weight unless otherwise specified.

EXAMPLE I

PREPARATION OF 2-ISOBUTYLIDENECYCLOHEXANONE

Reaction:

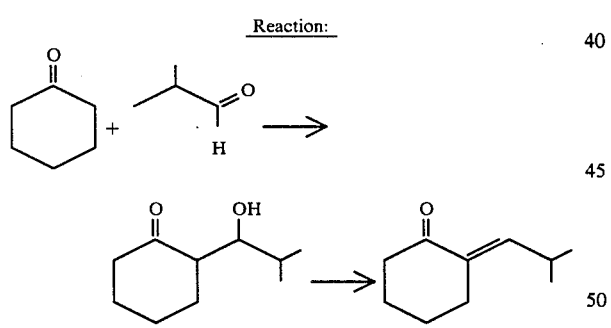

Into a 8 liter reaction vessel are placed 3400 grams cyclohexanone, 250 grams of water and 80 grams of sodium hydroxide. Over a period of one hour while maintaining the reaction mass at 50°-75° C., 1400 grams (19.4 moles) of isobutyraldehyde is added to the reaction mass. The reaction mass is stirred for a period of one hour. At the end of the one hour period, an equal volume of brine is added to the reaction mass. The organic phase is separated from the aqueous phase and the organic phase is washed with two volumes of brine. 500 ml Toluene is added to the organic phase and the water is azeotroped from the reaction mass. The reaction mass is then distilled yielding 1180 grams of product, the distillation taking place on a 2" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | — | — | — | — |
| 2 | 65 | 75 | 37.0 | 320 |
| 3 | 65 | 80 | 25.0 | 255 |
| 4 | — | — | — | 271 |
| 5 | 84 | 99 | 55.0 | 471 |
| 6 | 80 | 102 | 30.0 | 326 |
| 7 | 85 | 102 | 8.0 | 258 |
| 8 | 85 | 100 | 3.0 | 458 |
| 9 | 82 | 100 | 2.4 | 434 |
| 10 | 110 | 134 | 2.4 | 367 |
| 11 | 135 | 150 | 2.4 | 306 |
| 12 | 140 | 160 | 2.4 | 187 |
| 13 | 149 | 169 | 2.4 | 221 |
| 14 | 155 | 173 | 2.4 | 89 |
| 15 | 158 | 180 | 2.4 | 163 |

FIG. 1 is the GLC profile for the crude reaction product prior to distillation. The peak indicated by reference numeral 10 is the peak for the compound having the structure:

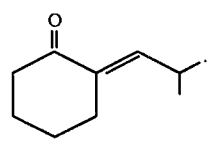

The peak indicated by reference numeral 11 is the peak for a compound having one of the structures:

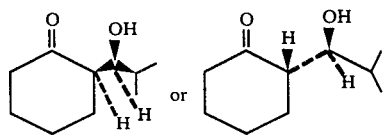

in admixture with other isomers. The peak indicated by reference numeral 12 is the peak for another one of the isomers having one of the structures:

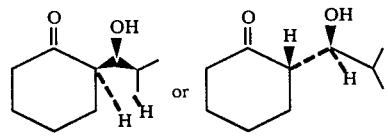

in admixture with a small amount of compound having the structure:

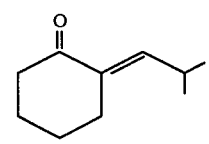

The peaks indicated by reference numerals 14 and 15 are the peaks for the compound having the structure:

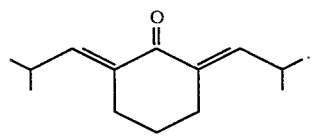

FIG. 2 is the NMR spectrum for the peak indicated by reference numeral 10 of FIG. 1, for the compound having the structure:

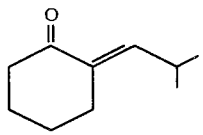

(Conditions: Field strength: 100 MHz; Solvent: CFCl₃).

FIG. 3 is the NMR spectrum for the peak indicated by reference numeral 11 on the GLC profile of FIG. 1, for one of the compounds having the structures:

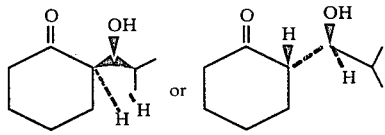

in admixture with other compounds (Conditions: Field strength: 100 MHz; Solvent: CFCl₃).

FIG. 4 is the NMR spectrum for the peak indicated by reference numeral 12 on the GLC profile of FIG. 1 for one of the compounds having the structures:

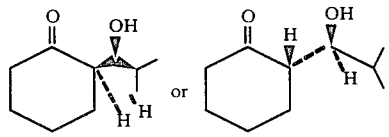

taken together with the compound having the structure:

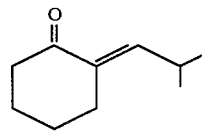

(Conditions: Field strength: 100 MHz; Solvent: CFCl₃).

FIG. 5 is the NMR spectrum for the peaks indicated by reference numerals 14 and 15 on the GLC profile of FIG. 1 for the compound having the structure:

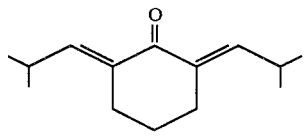

in admixture with other minor components (Conditions: Field strength: 100 MHz; Solvent: CFCl₃).

EXAMPLE II

PREPARATION OF 11-ISOPROPYL-9-METHYL SPIRO[5.5]UNDEC-8-EN-1-ONE

Reaction:

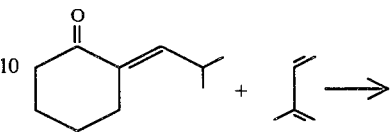

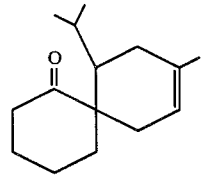

Into a 2000 ml reaction flask equipped with reflux condenser, addition funnel, heating mantle, thermowatch, nitrogen blanket apparatus and cooling bath are placed a mixture of 60 grams of aluminum chloride and 150 ml toluene. The resulting mixture is heated to 45° C. and over a period of 0.5 hours a mixture of 456 grams of the compound having the structure:

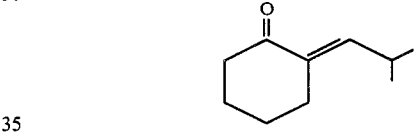

(prepared according to Example I, supra) and 150 ml toluene is added to the reaction mass.

Over a period of 0.5 hours, a mixture of 214 grams of isoprene and 150 ml toluene is then added to the reaction mass while maintaining the reaction at 40° C. The reaction mass is maintained at 40° C. for a period of three hours. At the end of the three hour period, the reaction mass is cooled to room temperature.

The reaction mass is then fractionally distilled yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 70 | 125 | 0.8 | 8.5 |
| 2 | 125 | 145 | 0.8 | 192.7 |
| 3 | 148 | 196 | 2.3 | 151.6 |

Fractions 1, 2 and 3 are bulked and redistilled yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | /113 | /137 | 3.2 | 2:1 |
| 2 | — | — | — | — |
| 3 | 125 | 136 | 2.8 | 2:1 |
| 4 | 125 | 137 | 2.8 | 3:1 |
| 5 | 125 | 137 | 2.6 | 9:1 |
| 6 | 126 | 138 | 2.6 | 9:1 |
| 7 | 126 | 139 | 2.6 | 2:1 |
| 8 | 127 | 141 | 2.8 | 2:1 |
| 9 | 127 | 143 | 2.8 | 2:1 |

-continued

| Fraction No. | Vapor Temp. (°C.) | Liquid Temp. (°C.) | Vacuum mm/Hg. Pressure | Reflux Ratio |
|---|---|---|---|---|
| 10 | 128 | 147 | 2.7 | 2:1 |
| 11 | 129 | 150 | 2.8 | 2:1 |
| 12 | 132 | 157 | 3.0 | 2:1 |
| 13 | 144 | 165 | 3.2 | 2:1 |
| 14 | 155 | 171 | 3.6 | 2:1 |
| 15 | 162 | 182 | 5.1 | 2:1 |
| 16 | 162 | 205 | 2.8 | 2:1 |

Distillation Fractions 4–8 are bulked and are found to have a woody, fruity, minty and floral aroma profile with pepper and geranium topnotes.

FIG. 6 is the GLC profile for the crude reaction product prior to distillation.

FIG. 7 is the GLC profile for bulked Fractions 1, 2 and 3 of the first distillation.

FIG. 8 is the GLC profile for bulked distillation Fractions 9 and 10 of the second distillation containing the compound having the structure:

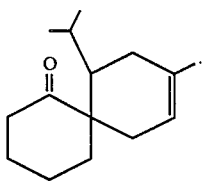

FIG. 9 is the NMR spectrum for Fraction 2 of the second distillation containing the compound having the structure:

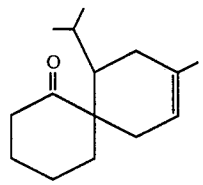

(Conditions: Field strength: 100 MHz; Solvent: CFCl₃).

EXAMPLE III

PREPARATION OF 3,3,5,9-TETRAMETHYL SPIRO[5,5]UNDEC-8-EN-1-ONE

Reaction:

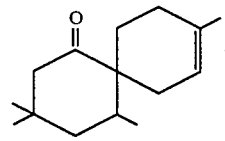

Into a 2 liter autoclave are charged the following materials:
(i) formaldehyde—240 grams;
(ii) dibutylamine—270 grams;
(iii) acetic acid—270 grams;
(iv) dihydroisophorone—280 grams; and
(v) isoprene—235 grams.

The autoclave is closed, sealed and heated to 160° C. and maintained at 160° C. for a period of five hours. At the end of the five hour period, the autoclave is cooled, depressurized and opened. The contents are removed and washed with saturated sodium chloride solution until neutral (3 volumes of saturated sodium chloride solution). The reaction mass is then washed with one volume of toluene. The reaction mass is then distilled on a 2" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | /61 | /83 | 1.0 | 277.5 |
| 2 | 59 | 84 | 3.2 | 83.9 |
| 3 | 110 | 127 | 3.0 | 181.0 |
| 4 | 153 | 127 | 2.4 | 185.3 |
| 5 | 169 | 204 | 2.6 | 237.5 |
| 6 | 150 | 222 | 2.6 | 40.1 |

(Yield: 34%).

FIG. 10 is the GLC profile for the crude reaction product prior to distillation (Conditions: Carbowax column programmed at 100°–220° C. at 8° C. per minute).

FIG. 11 is the GLC profile for the first distillation product (Conditions: Carbowax 20M column programmed at 100°–220° C. at 8° C. per minute). The peak indicated by reference numeral 110 is the peak for the compound having the structure:

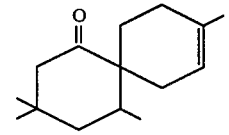

FIG. 12 is the NMR spectrum for the compound having the structure:

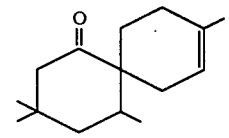

prepared according to this example (Conditions: Field strength: 100 MHz; Solvent: CFCl₃).

The compound having the structure:

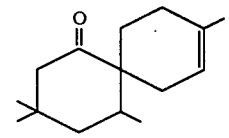

(bulked Fractions 6–8 of the foregoing distillation) has a woody, fresh minty, sweet, herbaceous, spicy and celery aroma profile with tagette-like undertones.

EXAMPLE IV(A)

PERFUME FORMULATIONS

The following "woody cologne" perfume formulation is prepared:

| Ingredients | Parts by York) | | |
|---|---|---|---|
| | IV(A) | IV(B) | IV(C) |
| Bergamot oil | 150 | 150 | 150 |
| Orange oil | 200 | 200 | 200 |
| Lemon oil | 50 | 50 | 50 |
| Eugenol | 10 | 10 | 10 |
| 4-(4-methyl-4-hydroxy amyl) $\Delta^3$ cyclohexene carboxaldehyde (LYRAL ® Trademark of International Flavors & Fragrances Inc. of New York, New York,) | 40 | 40 | 40 |
| Ylang oil | 2 | 2 | 2 |
| Petitgrain Paraguay | 10 | 10 | 10 |
| γ-Methyl ionone | 20 | 20 | 20 |
| Vetiver Venezuela | 18 | 18 | 18 |
| 3-α-Methyl-dodecahydro-6,6,9a-trimethylnaptho[2,1-b]furan | 5 | 5 | 5 |
| Product produced by the reaction of acetic anhydride, polyphosphoric acid and 1,5,9-trimethyl cyclododecatriene-1,5,9 according to the process of Example I of U.S. Pat. No. 3,718,697, the specification for which is incorporated by reference herein | 50 | 50 | 50 |
| Octahydro-9,9-dimethyl-1,6-methano-naphthalene-1-[2H]-ol produced according to Example III of U.S. Pat. No. 3,996,169, the specification for which is incorporated by reference herein | 50 | 50 | 50 |
| The compound having the structure: 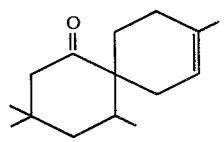 produced according to Example III, bulked distillation Fractions 6-8. | 12 | 0 | 0 |
| The compound having the structure: 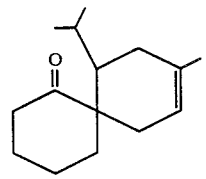 produced according to Example II, bulked distillation Fractions 4-8. | 0 | 12 | 0 |
| A 50:50 mixture of the compound having the structure: 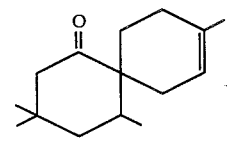 produced according to Example III, (bulked distillation Fractions 6-8); and | 0 | 0 | 12 |

-continued

| Ingredients | Parts by York) | | |
|---|---|---|---|
| | IV(A) | IV(B) | IV(C) |
| The compound having the structure: 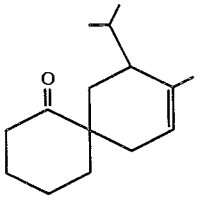 produced according to Example II, (bulked distillation Fractions 4-8). | | | |

The compound having the structure:

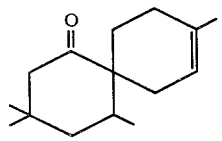

prepared according to Example III (bulked distillation Fractions 6-8) imparts a fresh minty, sweet, herbaceous, spicy and celery aroma with tagette-like undertones to the "woody cologne" composition of Example IV(A). Accordingly, the composition of Example IV(A) can be described as a "woody cologne" composition with fresh minty, sweet, herbaceous, spicy, celery and tagette-like undertones.

The compound having the structure:

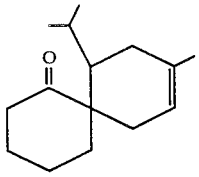

prepared according to Example II (bulked distillation Fractions 4-8) imparts to the "woody cologne" composition of Example IV(B) a fruity, minty and floral aroma with pepper and geranium topnotes. Accordingly, the composition of Example IV(B) can be described as a "woody cologne" composition with fruity, minty and floral undertones and pepper and geranium topnotes.

The 50:50 (weight:weight) mixture of compounds having the structure:

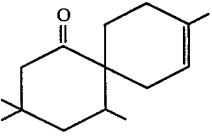

(produced according to Example III, bulked distillation Fractions 6-8) and the structure:

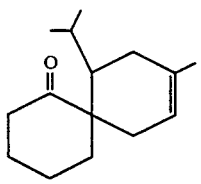

(produced according to Example II, bulked distillation Fractions 4–8) imparts to the "woody cologne" composition of Example IV(C), a woody, fruity, fresh minty, sweet, floral, herbaceous, spicy and celery aroma with pepper and geranium topnotes and tagette-like undertones. Accordingly, the "woody cologne" composition of Example IV(C) can be described as a "woody cologne" with fruity, fresh minty, sweet, floral, herbaceous, spicy, celery and tagette-like undertones and pepper and geranium topnotes.

EXAMPLE V

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
| --- | --- |
| The compound having the structure:<br>(structure image)<br>prepared according to Example II (bulked distillation Fractions 4–8). | A woody, fruity, minty and floral aroma with pepper and geranium topnotes. |
| The compound having the structure:<br>(structure image)<br>prepared according to Example III (bulked distillation Fractions 6–8). | A woody, fresh minty, sweet, herbaceous, spicy and celery aroma with tagette-like undertones. |
| Perfume composition of Example IV(A). | A "woody cologne" composition with fresh minty, sweet, herbaceous, spicy, celery and tagette-like undertones. |
| Perfume composition of Example IV(B). | A "woody cologne" composition with fruity, minty and floral undertones and pepper and geranium topnotes. |
| Perfume composition of Example IV(C). | A "woody cologne" with fruity, fresh minty, sweet, floral, herbaceous, spicy, celery and tagette-like undertones and pepper and geranium topnotes. |

EXAMPLE VI

PERFUMED LIQUID DETERGENTS

Concentrated liquid detergents (Lysine salt of n-dodecylbenzene sulfonic acid as more specifically described in U.S. Pat. No. 3,948,818, issued on Apr. 6, 1976 incorporated by reference herein) with aroma nuances as set forth in Table II of Example V, are prepared containing 0.10%, 0.15%, 0.20%, 0.25%, 0.30% and 0.35% of the substance set forth in Table II of Example V. They are prepared by adding and homogeneously mixing the appropriate quantity of substance set forth in Table II of Example V in the liquid detergent. The detergents all possess excellent aromas as set forth in Table II of Example V, the intensity increasing with greater concentrations of substances as set forth in Table II of Example V.

EXAMPLE VII

PREPARATION OF COLOGNES AND HANDKERCHIEF PERFUMES

Compositions as set forth in Table II of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example V are imparted to the colognes and to the handkerchief perfumes at all levels indicated.

EXAMPLE VIII

PREPARATION OF SOAP COMPOSITIONS

One hundred grams of soap chips [per sample] (IVORY ®, produced by the Procter & Gamble Company of Cincinnati, Ohio), are each mixed with one gram samples of substances as set forth in Table II of Example V until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example V.

EXAMPLE IX

PREPARATION OF SOLID DETERGENT COMPOSITIONS

Detergents are prepared using the following ingredients according to Example I of Canadian Patent No. 1,007,948 (incorporated by reference herein):

| Ingredient | Percent By Weight |
| --- | --- |
| "NEODOL" ® 45-11 (a C-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example V. Each of the detergent samples has an excellent aroma as indicated in Table II of Example V.

EXAMPLE X

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and their perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
57% $C_{20-22}$ HAPS
22% isopropyl alcohol;
20% antistatic agent
1% of one of the substances as set forth in Table II of Example V.

Fabric softening compositions prepared according to Example I at column 15 of U.S. Pat. No. 3,632,396 having the aroma characteristics as set forth in Table II of Example V, supra, consist of a substrate coating having a weight of about 3 grams per 100 square inches of substrate a first coating located directly on the substrate coating consisting of about 1.85 grams per 100 square inches of substrate; and an outer coating coated on the first coating consisting of about 1.4 grams per 100 square inches of substrate. One of the substances of Table II of Example V is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example V, supra.

EXAMPLE XI

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% of food grade ethanol. 8.0 Grams of the polymer is dissolved in the alcohol. The following ingredients are added to the PVP/VA alcoholic solution:

| Ingredient | Percent by Weight |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example V, supra. | 0.10 |

The perfuming substances as set forth in Table II of Example V add aroma characteristics as set forth in Table II of Example V which are rather intense and aesthetically pleasing to the users of the soft-feel, good-hold pump hair sprays.

EXAMPLE XII

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepen Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A & COMPOSITION B are then mixed in a 50:50 weight ratio of A:B and cooled to 45° C. and 0.3 weight percent of perfuming substance as set forth in Table II of Example V is added to the mixture. The resulting mixture is cooled to 40° C. and blending is carried out for an additional one hour in each case. At the end of this blending period, the resulting material has a pleasant fragrance as indicated in Table II of Example V.

What is claimed is:
1. An alkyl-substituted spiroundecenone derivative defined according to the structure:

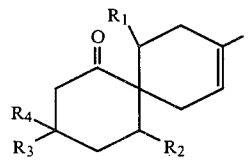

wherein $R_1$ is isopropyl or hydrogen; and $R_2$, $R_3$ and $R_4$ are each the same and each represents methyl or hydrogen with the provisos:
(i) when $R_1$ is isopropyl then $R_2$, $R_3$ and $R_4$ are each hydrogen; and
(ii) when $R_2$, $R_3$ and $R_4$ are each methyl then $R_1$ is hydrogen.

2. A process for augmenting or enhancing the aroma of a consumable material selected from the group consisting of perfume compositions, colognes and perfumed articles comprising the step of adding to said consumable material, an aroma augmenting or enhancing quantity of the product of claim 1.

3. The product of claim 1 having the structure:

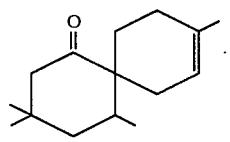

4. The product of claim 1 having the structure:

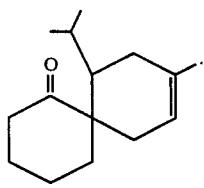

5. The process of claim 2 wherein the consumable material is a perfume composition and the alkyl-substituted spiroundecenone derivative has the structure:

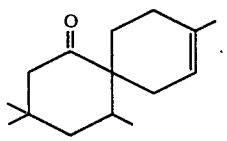

6. The process of claim 2 wherein the consumable material is a perfume composition and the alkyl-substituted spiroundecenone derivative has the structure:

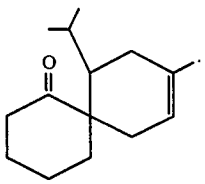

7. The process of claim 2 wherein the consumable material is a perfumed article and the perfumed article is a solid or liquid anionic, cationic, nonionic or zwitterionic detergent.

8. The process of claim 2 wherein the consumable material is a fabric softener composition or fabric softener article.

9. The process of claim 2 wherein the consumable material is a perfumed article and the perfumed article is a hair preparation.

* * * * *